US008744557B2

(12) United States Patent
Sternickel et al.

(10) Patent No.: US 8,744,557 B2
(45) Date of Patent: *Jun. 3, 2014

(54) USE OF MACHINE LEARNING FOR CLASSIFICATION OF MAGNETO CARDIOGRAMS

(71) Applicant: CardioMag Imaging, Inc., Latham, NY (US)

(72) Inventors: Karsten Sternickel, Bonn (DE); Boleslaw Szymanski, Newtonville, NY (US); Mark Embrechts, Clifton Park, NY (US)

(73) Assignee: Cardio Mag Imaging, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/772,138

(22) Filed: Feb. 20, 2013

(65) Prior Publication Data

US 2013/0178730 A1 Jul. 11, 2013

Related U.S. Application Data

(63) Continuation of application No. 12/819,095, filed on Jun. 18, 2010, now Pat. No. 8,391,963, which is a continuation of application No. 10/561,285, filed as application No. PCT/US2004/021307 on Jul. 1, 2004, now Pat. No. 7,742,806.

(60) Provisional application No. 60/483,961, filed on Jul. 1, 2003.

(51) Int. Cl.
 *A61B 5/04* (2006.01)

(52) U.S. Cl.
 USPC .......................................... 600/509

(58) Field of Classification Search
 USPC .......................................... 600/509
 See application file for complete search history.

(56) References Cited

U.S. PATENT DOCUMENTS

| 4,958,638 | A | 9/1990 | Sharpe et al. |
| 5,092,343 | A | 3/1992 | Spitzer et al. |

(Continued)

FOREIGN PATENT DOCUMENTS

| WO | 2005002313 A2 | 1/2005 |
| WO | 2005002313 A3 | 1/2005 |

OTHER PUBLICATIONS

A. Bezerianos, L. Vladutu, S. Papadimitriou, Hierarchical state space partitioning with a network self-organising map for the recognition of ST-T segment changes, Med. Biol. Eng. Comput., 2000, 406-415.

(Continued)

*Primary Examiner* — George Manuel
(74) *Attorney, Agent, or Firm* — Jay R. Yablon

(57) ABSTRACT

The use of machine learning for pattern recognition in magnetocardiography (MCG) that measures magnetic fields emitted by the electrophysiological activity of the heart is disclosed herein. Direct kernel methods are used to separate abnormal MCG heart patterns from normal ones. For unsupervised learning, Direct Kernel based Self-Organizing Maps are introduced. For supervised learning Direct Kernel Partial Least Squares and (Direct) Kernel Ridge Regression are used. These results are then compared with classical Support Vector Machines and Kernel Partial Least Squares. The hyper-parameters for these methods are tuned on a validation subset of the training data before testing. Also investigated is the most effective pre-processing, using local, vertical, horizontal and two-dimensional (global) Mahanalobis scaling, wavelet transforms, and variable selection by filtering.

20 Claims, 7 Drawing Sheets

(56) References Cited

U.S. PATENT DOCUMENTS

| | | |
|---|---|---|
| 5,280,792 A | 1/1994 | Leong et al. |
| 5,417,211 A | 5/1995 | Abraham-Fuchs et al. |
| 5,436,447 A | 7/1995 | Shew |
| 5,465,308 A | 11/1995 | Hutcheson et al. |
| 5,680,866 A | 10/1997 | Kangas et al. |
| 5,819,007 A | 10/1998 | Elghazzawi |
| 5,827,195 A | 10/1998 | Lander |
| 6,128,608 A | 10/2000 | Barnhill |
| 6,210,344 B1 | 4/2001 | Perin et al. |
| 6,248,063 B1 | 6/2001 | Barnhill et al. |
| 6,342,699 B1 | 1/2002 | Jeanguillaume |
| 6,443,889 B1 | 9/2002 | Groth et al. |
| 6,572,560 B1 | 6/2003 | Watrous et al. |
| 6,714,925 B1 | 3/2004 | Barnhill et al. |
| 6,728,691 B1 | 4/2004 | Neuneier et al. |
| 6,827,695 B2 | 12/2004 | Palazzolo et al. |
| 7,742,806 B2 | 6/2010 | Sternickel et al. |
| 8,391,963 B2 | 3/2013 | Sternickel et al. |
| 2002/0165837 A1 | 11/2002 | Zhang et al. |
| 2007/0167846 A1 | 7/2007 | Sternickel et al. |
| 2011/0047105 A1 | 2/2011 | Sternickel et al. |

OTHER PUBLICATIONS

M. E. Tagluk, M. J. English, The Analysis of ECG Signals Using Time-Frequency Techniques, Proceedings, 19th International Conference, IEEE/EMBS Oct. 30-Nov. 2, 1997, Chicago, IL, USA.

S. Jankowski, J. Tijink, G. Vumbaca, M. Balsi, G. Karpinski, Support Vector Machine for the Recognition of Atrial and Ventricular Depolarization in Holter ECG Recording, International Journal of Bioelectromagnetism, 2002, vol. 4, No. 2, pp. 343-344.

J. Millet-Roig, R. Ventura-Galiano, F. J. Chorro-Gasco, A. Cebrian, Support Vector Machine for Arrhythmia Discrimination with Wavelet-Transform-Based Feature Selection, Computers in Cardiology 2000:27:407-410.

Bennett, K.P. and Embrechts M.J., An Optimization Perspective on Kernel Partial Least Squares Regression, in Suykens, J.A.K., Horvath, G., Basu, S., Micchelli, C., Vandewalle J. (Eds.), Advances in Learning Theory: Methods, Models and Applications, NATO Science Series III: Computer & Systems Sciences, vol. 190, IOS Press Amsterdam, Jan. 2003, 436pp. (ISBN: 1 58603 341 7).

| Method | %correct | #misses | time (s) |
|---|---|---|---|
| SVMLib | 74 | 4+5 | 10 |
| K-PLS | 74 | 4+5 | 6 |
| DK-PCA | 71 | 7+3 | 5 |
| PLS | 63 | 2+11 | 3 |
| K-PLS | 80 | 2+5 | 6 |
| DK-PLS | 80 | 2+5 | 5 |
| SVMLib | 80 | 2+5 | 10 |
| LS-SVM | 80 | 2+5 | 0.5 |
| SOM | 63 | 3+10 | 960 |
| DK-SOM | 71 | 5+5 | 28 |
| DK-SOM | 77 | 3+5 | 28 |

| Method | q2 | Q2 | RMSE |
|---|---|---|---|
| SVMLib | 0.767 | 0.842 | 0.852 |
| K-PLS | 0.779 | 0.849 | 0.856 |
| DK-PCA | 0.783 | 0.812 | 0.87 |
| PLS | 0.841 | 0.142 | 1.146 |
| K-PLS | 0.591 | 0.694 | 0.773 |
| DK-PLS | 0.591 | 0.694 | 0.773 |
| SVMLib | 0.591 | 0.697 | 0.775 |
| LS-SVM | 0.59 | 0.692 | 0.772 |
| SOM | 0.866 | 1.304 | 1.06 |
| DK-SOM | 0.855 | 1.0113 | 0.934 |
| DK-SOM | 0.755 | 0.859 | 0.861 |

| Method | Domain | RMSE | CC [%] |
|---|---|---|---|
| SVMLib | time | 0.852 | 74 |
| K-PLS | time | 0.856 | 74 |
| DK-PCA | D4-wavelet | 0.87 | 71 |
| PLS | D4-wavelet | 1.146 | 63 |
| K-PLS | D4-wavelet | 0.773 | 80 |
| DK-PLS | D4-wavelet | 0.75 | 83 |
| SVMLib | D4-wavelet | 0.775 | 80 |
| LS-SVM | D4-wavelet | 0.772 | 80 |
| SOM | D4-wavelet | 1.06 | 63 |
| DK-SOM | D4-wavelet | 0.861 | 77 |

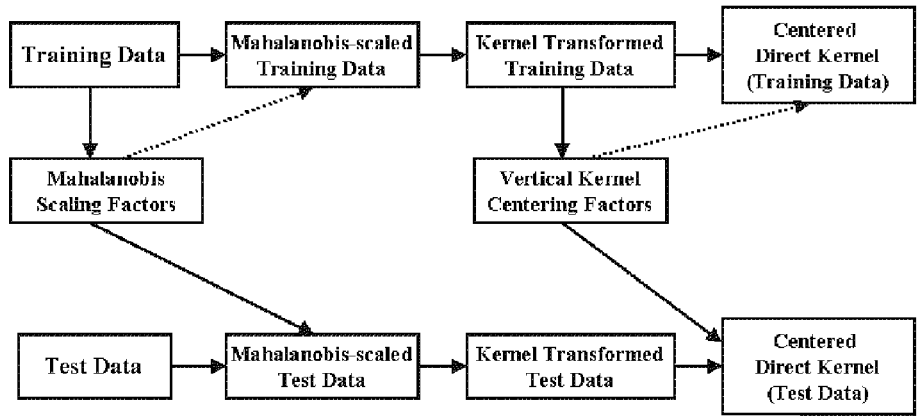
Figure 10
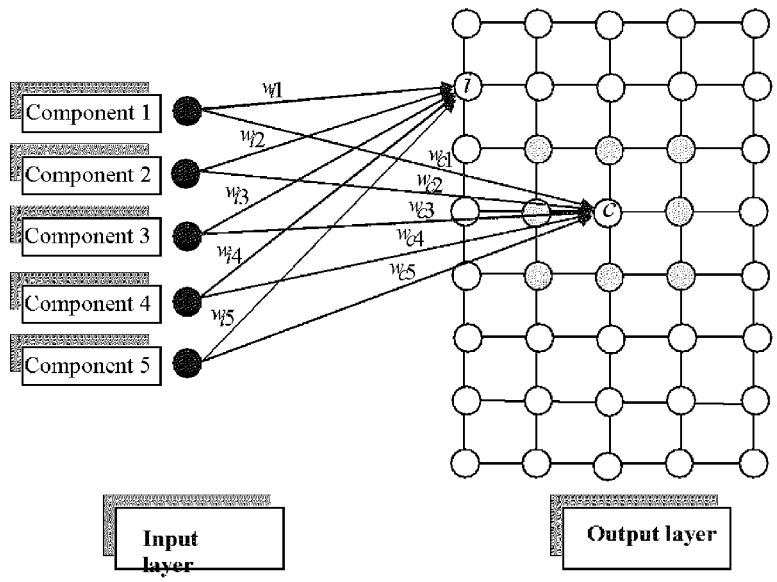
Figure 11
| Linear methods | Non-linear kernel methods | Newly developed methods |
|---|---|---|
| PLS | SVMLib | DK-SOM |
| PCA | SOM | DK-PLS |
|  | LS-SVM | DK-PCA |
|  | K-PLS |  |
Figure 12

USE OF MACHINE LEARNING FOR CLASSIFICATION OF MAGNETO CARDIOGRAMS

CROSS-REFERENCE TO RELATED APPLICATIONS

This application is a continuation of U.S. Ser. No. 12/819,095 filed Jun. 19, 2010, now U.S. Pat. No. 8,391,963 issued Mar. 5, 3013. Said U.S. Ser. No. 12/819,095 is a continuation of U.S. Ser. No. 10/561,285 filed Dec. 20, 2005, now U.S. Pat. No. 7,742,806 issued Jun. 22, 2010. Said U.S. Ser. No. 10/561,285 is a US national stage application of PCT/US04/21,307 filed Jul. 1, 2004, which in turn claims benefit of U.S. 60/483,961 filed Jul. 1, 2003. The foregoing are all hereby incorporated by reference.

BACKGROUND OF THE INVENTION

Although magnetocardiography (MCG) was introduced in the early 1960's as a possible diagnostic tool, it took almost thirty years to successfully demonstrate its clinical value. Today, it represents one of the emerging new technologies in cardiology employed by physicians in hospitals around the world. The clinical application of MCG method has significantly benefited from modern multichannel sensor technology, sophisticated software, as well as from recent improvements in hardware allowing the use of the device without a magnetically-shielded room.

MCG studies are fast, safe and completely noninvasive. Consequently, this offers great convenience for the patient. Currently, many groups work on establishing libraries of reference data and data standardization. There are several clinical applications for which MCG has already provided clinically-useful results. For example, MCG can diagnose and localize acute myocardial infarctions, separate myocardial infarction patients with and without susceptibility of malignant ventricular arrhythmias, detect ventricular hypertrophy and rejection after heart transplant, localize the site of ventricular pre-excitation and many types of cardiac arrhythmias, as well as reveal fetal arrhythmias and conduction disturbances [40]. In addition, several other clinical applications of MCG have recently been studied: detection and risk stratification of cardiomyopathies (dilated, hypertrophic, arrhythmogenic, diabetic), risk stratification after idiopathic ventricular fibrillation, detection and localization of myocardial viability, and follow-up of fetal growth and neural integrity. Some studies have clearly indicated that MCG is very sensitive to changes in repolarization, e.g., after myocardial infarction or in a hereditary long-QT syndrome [42]. The most relevant overview of MCG applications and currently-used analysis techniques can be found in [41].

An important challenge, however, is to reduce or eliminate the variability introduced by human interpretation of MCG data, and to significantly improve the machine-based classification performance and quality of generalization, while maintaining computer processing times that are compatible with real-time diagnosis.

Three basic steps are always performed when applying artificial intelligence (machine learning) to measured data: 1. measurement of the data, 2. pre-processing of the measured data, 3. training of the adaptive classifier. Patents incorporating this basic approach to EKG/ECG data or other biological data include U.S. Pat. Nos. 5,092,343; 5,280,792; 5,465,308; 5,680,866; 5,819,007; 6,128,608; 6,248,063; 6,443,889; 6,572,560; 6,714,925; and 6,728,691.

The use of artificial intelligence for analysis of MCG field patterns is quite limited to date. One reference for the application of artificial intelligence for analysis of biomagnetic signals is U.S. Pat. No. 5,417,211, which discloses a method for classifying field patterns generated by electrophysiological activities occurring inside the body of a living subject including the steps of measuring field patterns arising as a result of the electrophysiological activities outside the body of the subject using a multi-channel measuring apparatus, generating feature vectors corresponding to the measured field patterns, supplying the feature vectors to an adaptive classifier, and training the adaptive classifier with training field patterns which have been generated by a localizable surrogate model of the electrophysiological activity. The method includes the further step of generating a probability value for each field pattern at an output of the adaptive classifier which indicates the probability with which each field pattern can be generated by a selected localizable surrogate model Like the EKG/ECG references cited above, this discusses the general applicability of machine learning to the measured data, but does not present the specifics of how to improve the classification performance and quality of generalization.

In all cases, the two key measures which determine success are the classification performance and quality of generalization. While training on non-optimally pre-processed data leads to poor classification results, so-called overtraining prevents the adaptive classifier from generalizing to the proper recognition of real-world data.

The key to success lies in an optimal pre-processing of the data, which has not yet been achieved to date by any of the references cited herein. It is critically important to identify all features that determine the class to which the investigated dataset belongs. It is neither obvious nor trivial to identify those features. Moreover, these features may vary from biological system to biological system, and from one type of measured data to another. In consequence, most artificial intelligence based procedures differ in how the pre-processing is performed.

As will be disclosed in detail herein, the use of kernel transforms and wavelet transforms to preprocess data for machine learning provides the basis for a successful machine learning approach which significantly improves on the prior art in terms of accurate classification, quality of generalization, and speed of processing. This has not been disclosed or suggested in any of the prior art cited herein.

SUMMARY OF THE INVENTION

The use of machine learning for pattern recognition in magnetocardiography (MCG) that measures magnetic fields emitted by the electrophysiological activity of the heart is disclosed herein. Direct kernel methods are used to separate abnormal MCG heart patterns from normal ones. For unsupervised learning, Direct Kernel based Self-Organizing Maps are introduced. For supervised learning Direct Kernel Partial Least Squares and (Direct) Kernel Ridge Regression are used. These results are then compared with classical Support Vector Machines and Kernel Partial Least Squares. The hyper-parameters for these methods are tuned on a validation subset of the training data before testing. Also investigated is pre-processing, using local, vertical, horizontal and two-dimensional (global) Mahanalobis scaling, wavelet transforms, and variable selection by filtering. The results, similar for all three methods, were encouraging, exceeding the quality of classification achieved by the trained experts.

Disclosed herein is a device and associated method for classifying cardiography data, comprising applying a kernel transform to sensed data acquired from sensors sensing electromagnetic heart activity, resulting in transformed data, prior to classifying the transformed data using machine learning.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) summarized below.

FIG. 10 is a flow diagram illustrating data pre-processing with kernel centering for direct kernel methods.

FIG. 11 is typical structure of a self-organizing map (SOM).

FIG. 12 is a list of techniques disclosed herein for the automatic classification of cardiograph data.

DETAILED DESCRIPTION

Figures 1, 2, 3:
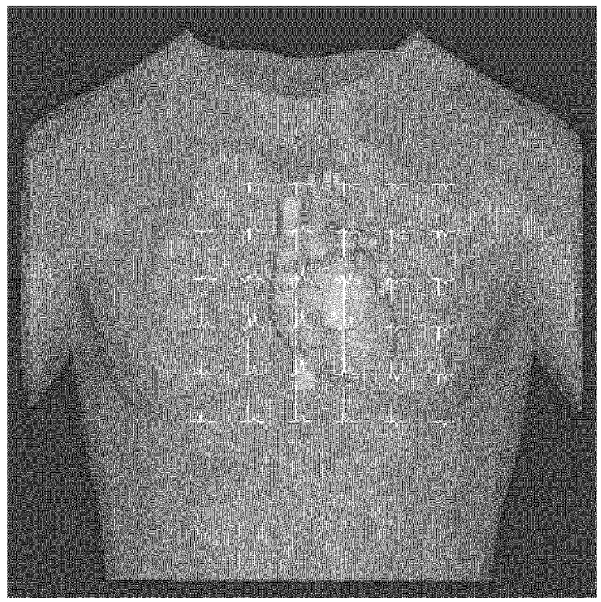
FIG. 1 illustrates filtered and averaged temporal MCG traces over one cardiac cycle collected in 36 channels comprising a 6×6 grid.
FIG. 2 is a chart illustrating numbers of correct patterns and misses (for negative and positive cases on 36 test data) as well as execution times for magnetocardiogram data. Support vector machine library (SVMLib) and kernel partial least square (K-PLS) use time domain and the remaining methods use D-4 wavlet domain.
FIG. 3 is a chart illustrating quality measures for different methods for creating predictive models for magneto-cardiogram data.

This disclosure describes the use of direct-kernel methods and support vector machines for pattern recognition in magnetocardiography (MCG) that measures magnetic fields emitted by the electrophysiological activity of the human heart. A SQUID-based measuring device for MCG that can be used in regular hospital rooms (not specially shielded from electromagnetic interference) is presently under separate development. The operation of the system is computer-controlled and largely automated. Proprietary software is used for precise 24-bit control and data acquisition followed by filtering, averaging, electric/magnetic activity localization, heart current reconstruction, and derivation of diagnostic scores.

The interpretation of MCG recordings remains a challenge. Hence, this disclosure considers the methods to automate interpretation of MCG measurements to minimize human input for the analysis. Testing has focused on detecting ischemia, a condition arising in many common heart diseases that may result in heart attack, the leading cause of death in the United States, but this exemplary, not limiting.

Scientifically, this disclosure considers a two-class separation problem (diseased heart vs. healthy heart) where the number of descriptors (data points) exceeds the number of datasets. Hence, this disclosure focuses now on two tasks for the solution of this problem.

The first question to be answered is whether the problem is linear or non-linear because this determines the class of possible candidate functions that can solve the problem (known as "hypotheses" or "machine learning techniques"). Our goal is to keep the separation process itself linear and encode non-linearities, if any, in the pre-processing. The latter can be achieved by applying a (non-linear) kernel transformation to the data prior to performing the actual machine learning (we refer to techniques that operate on kernel transformed data as "non-linear" techniques). Hence, if the data contain non-linearities, purely linear methods will show an inferior performance compared to non-linear techniques.

The second objective is to find (or develop) machine learning techniques that actually solve the separation problem. The focus here is not so much on finding the best solution but a class of techniques that perform equally well on the data. This helps to build confidence in the chosen models and their generalization capabilities (the ability of a hypothesis to correctly classify data not in the training set is known as its "generalization"). It is easy to develop a model that performs optimally on the training data but cannot predict unseen data (the phenomenon often referred to as overtraining). It is very difficult, however, to build (and tune) a model with good prediction based on only few data.

We start with a discussion of data acquisition and preprocessing. Particularly, we discuss what kind of preprocessing is suitable to different learning methods. Thereafter we present the core results: the comparison of performance of different machine learning techniques for our problem, and methodologies for assessment of prediction quality and for the regularization parameter selection. Thereafter we discuss feature selection.

Data Acquisition and Pre-Processing

MCG data are acquired at 36 locations above the torso by making four sequential measurements in mutually adjacent positions. In each position the nine sensors measure the cardiac magnetic field for 90 seconds using a sampling rate of 1000 Hz leading to 36 individual time series. For diagnosis of ischemia, a bandwidth of 0.5 Hz to 20 Hz is needed, so a hardware low pass filter at 100 Hz using 6th-order Bessel filter characteristics is applied, followed by an additional digital low pass filter at 20 Hz using the same characteristics, but a higher order. To eliminate remaining stochastic noise components, the complete time series is averaged using the maximum of the R peak of the cardiac cycle as a trigger point. For automatic classification, we used data from a time window between the J point and T peak [5] of the cardiac cycle in which values for 32 evenly spaced points were interpolated from the measured data. The training data consist of 73 cases that were easy to classify visually by trained experts. The testing was done on a set of 36 cases that included patients whose magnetocardiograms misled or confused trained experts doing visual classification.

Data were preprocessed in this case by first subtracting the bias from each signal. Then, we investigated the most effective pre-processing for our multi-variate time-series signals, including local, vertical, horizontal and two-dimensional (global) Mahanalobis scaling, and wavelet transforms. An important consideration was preservation of data locality, which was achieved by applying to each signal the Daubechies-4 wavelet transform [3]. It was chosen, because of the relatively small set of data (32) in each of the interpolated time signals. Only SOM and K-PLS methods that observe data locality in input did not require this transformation. Next, we Mahalanobis scaled the data, first on all 36 signals and then (for all except SOM based methods) vertically. A typical dataset for 36 signals that are interpolated to 32 equally spaced points in the ST segment [5] and after Mahalanobis scaling on each of the individual signals is shown in FIG. 1.

Predicitive Modeling for MCG Data Classification

The aim of machine learning is to delegate some basics of intelligent decision making to computers. In its current form a significant part of machine learning is based on the development of robust classification, regression tools and feature selection methods.

The ultimate aim of machine learning in the context of cardiac diagnosis is to be able to identify meaningful features that can explain the model and allow the formulation of expert rules that have transparency.

A key ingredient of machine learning is the prevention of overtraining. The concept of Tikhonov regularization is a powerful concept in machine learning for doing so. A second issue in machine learning is the need for building reliable nonlinear methods. Support vector machines (SVMs) and other kernel-based methods, such as kernel principal component analysis, kernel ridge regression, and partial least squares are powerful methods for incorporating non-linearity and regularization in machine learning methods.

Current challenges in machine learning are in large problems with more features than data, problems with lots of uncertainty and noise in the data, and non-ordinal multi-class classification problems with mixture modes.

The need for proper pre-processing is highly domain dependent, but exploring different pre-processing methods, and incorporating domain expertise in this pre-processing stage is a key ingredient to making machine learning methods work.

Our purpose is to identify not only "the best" machine learning method but also a class of techniques that perform equally well on the data. Therefore, we consider SVMs, a prime tool in the machine learning community. We also use other kernel based methods that might be easier to tune or easier to implement in hardware than SVMs, but were expected to perform comparably to SVMs.

One key for successful machine learning lies in the pre-processing of the data. Many different pre-processing scenarios are worthy of consideration. We distinguish among four types of preprocessing as follows:
1. Normalization: this is needed to make the data comparable. It usually means that the data are scaled and de-biased. However, one has many choices here.
2. Localization of information: by localization we mean applying a transform that rearranges the data such that the coefficients, which contain most of the information, are presented first. One prominent example is the Wavelet Transform that even preserves locality of information.
3. Feature selection: this usually operates on already transformed data. It means that coefficients that either contain no or little information are cut out to reduce the dimensionality of the input domain. This is particularly useful to speed up the learning.
4. Kernel transformation: The kernel transformation is an elegant way to make a regression model nonlinear. A kernel is a matrix containing similarity measures for a dataset: either between the data of the dataset itself, or with other data (e.g., support vectors [2]).

It is clear that this offers a variety of combinations of approaches for improving cardiogram classification.

Turning first to normalization, It is a common procedure in machine learning to center all the descriptors and to bring them to a unity variance. The same process is then applied to the response. This procedure of centering and variance normalization is known as Mahalanobis scaling. While Mahalanobis scaling is not the only way to pre-process the data, it is probably the most general and the most robust way to do pre-processing that applies well across the board. If we represent a feature vector as $\vec{z}$, Mahalanobis scaling will result in a rescaled feature vector $\vec{z}'$ and can be summarized as:

$$\vec{z}' = \frac{\vec{z} - \bar{z}}{std(\vec{z})} \qquad (1)$$

where $\bar{z}$ represents the average value and std ($\vec{z}$) represents the standard deviation for attribute $\vec{z}$.

We will refer to "horizontal Mahalanobis scaling" when the 36 time series are scaled individually (along the time axis), to "vertical Mahalanobis scaling" when all 36 points at one instance of time are scaled, and to "global Mahalanobis scaling" when all 36 points at all 32 time instances are scaled.

We turn next to localization. Applying a Wavelet transform [10] helps to localize "hot spots" of information on the one hand and "cold areas" that don't contribute to the signal on the other hand. The property that makes the Wavelet transform more suitable than a Fourier transform is that individual wavelet functions are localized in space. Fourier sine and cosine functions are not. Wavelet transforms do not have a single set of basis functions but an infinite set of possible basis functions.

Dilations and translations of the "Mother function," or "analyzing wavelet" $\Phi(x)$ define an orthogonal basis, also known as the wavelet basis:

$$\Phi(s, l) = 2^{\frac{-s}{2}} \Phi(2^{-s}x - l) \qquad (2)$$

The variables s and l are integers that scale and dilate the mother function $\Phi(x)$ to generate wavelets, such as a Daubechies wavelet family. The scale index s indicates the wavelet's width, and the location index l gives its position. Notice that the mother functions are rescaled, or "dilated" by powers of two, and translated by integers. What makes wavelet bases especially interesting is the self-similarity caused by the scales and dilations. Once we know about the mother functions, we know everything about the basis.

To span our data domain at different resolutions, the analyzing wavelet is used in a scaling equation:

$$W(x) = \sum_{k=-1}^{N-2} (-1)^k c_{k+1} \Phi(2x + k) \qquad (3)$$

where W(x) is the scaling function for the mother function $\Phi(x)$, and $c_k$ are the wavelet coefficients. The wavelet coeffi cients must satisfy linear and quadratic constraints of the form $$\sum_{k=0}^{N-1} c_k = 2, \sum_{k=0}^{N-1} c_k c_{k+2l} = 2\delta_{l,0} \qquad (4)$$

where $\delta$ is the delta function and l is the location index.

One of the most useful features of wavelets is the ease with which a scientist can choose the defining coefficients for a given wavelet system to be adapted for a given problem. In Daubechies' paper [3], she developed specific families of wavelet systems that were very good for representing polynomial behavior. For MCG time series, the so-called "Daubechies 4" wavelet showed optimal performance.

We turn now to the kernel transform. The kernel transform and its tuning is an important component of the ability to improve cardiogram classification. Therefore, we will explain this concept in more detail and pinpoint some major problems which are commonly overlooked when applying kernel transforms.

The kernel transformation is an elegant way to make a regression model nonlinear. The kernel transformation goes back at least to the early 1900's, when Hilbert introduced kernels in the mathematical literature. A kernel is a matrix containing similarity measures for a dataset: either between the data of the dataset itself, or with other data. A classical use of a kernel is as the correlation matrix in principal component analysis, where the feature kernel contains linear similarity measures between attributes or features. In support vector machines, the kernel entries are similarity measures between data rather than features and these similarity measures are usually nonlinear. There are many possible nonlinear similarity measures, but in order to be mathematically tractable the kernel has to satisfy certain conditions, the so-called Mercer conditions [2, 11, 15].

$$\overleftrightarrow{K}_{nn} = \begin{bmatrix} k_{11} & k_{12} & \ldots & k_{1n} \\ k_{21} & k_{22} & \ldots & k_{2n} \\ & & \ldots & \\ k_{n1} & k_{n2} & \ldots & k_{nn} \end{bmatrix} \qquad (5)$$

The expression above, introduces the general structure for the data kernel matrix, $\overleftrightarrow{K}_{nm}$, for n data. The kernel matrix is a symmetrical matrix where each entry contains a (linear or nonlinear) similarity between two data vectors. There are many different possibilities for defining similarity metrics such as the dot product, which is a linear similarity measure and the Radial Basis Function kernel or RBF kernel, which is a nonlinear similarity measure. The RBF kernel is the most widely used nonlinear kernel and its entries are defined by $$k_{ij} \equiv e^{-\frac{\|\vec{x}_j - \vec{x}_i\|_2}{2\sigma^2}} \qquad (6)$$

Note that in the kernel definition above, the kernel entry contains the Euclidean distance between data points, which is a dissimilarity (rather than a similarity) measure, in a negative exponential. The negative exponential also contains a free parameter, $\sigma$, which is the Parzen window width for the RBF kernel. The proper choice for selecting the Parzen window is usually determined by an additional tuning, also called hyper-tuning, on an external validation set. The precise choice for $\sigma$ is not crucial, there usually is a relatively broad range for the choice for $\sigma$ for which the model quality is stable.

The kernel transformation is applied here as a data transformation in a separate pre-processing stage. We actually replace the data by a nonlinear data kernel and apply a traditional linear predictive model. Methods where a traditional linear algorithm is used on a nonlinear kernel transform of the data are introduced and defined here as "direct kernel methods." The elegance and advantage of such a direct kernel method is that the nonlinear aspects of the problem are captured in the kernel and are transparent to the applied algorithm.

Figure 9:
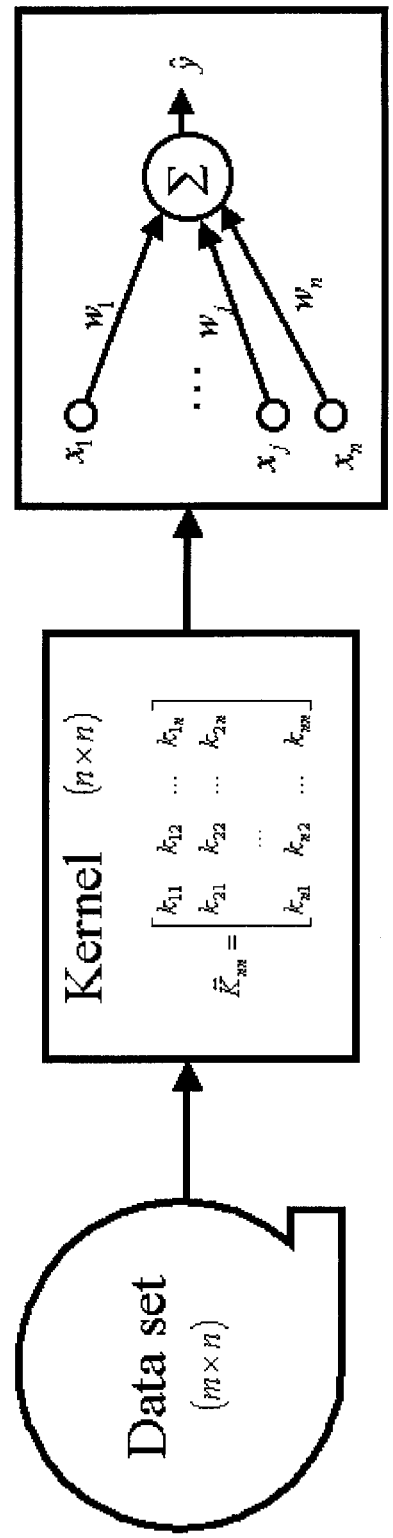
FIG. 9 is an operation schematic for direct kernel methods as a data pre-processing step.

One could also represent the kernel transformation in a neural network type of flow diagram and the first hidden layer would now yield the kernel-transformed data, and the weights in the first layer would be just the descriptors of the training data. The second layer contains the weights that can be calculated with a numerical method, such as kernel ridge regression (see FIG. 9). When a radial basis function kernel is used, this type of neural network would look very similar to a radial basis function neural network [17,18], except that the weights in the second layer are calculated differently.

It is also important to deal with bias by centering the Kernel. Looking at the general prediction equation $$\hat{\vec{y}}_n = X_{nm} \vec{w}_m \qquad (7)$$

in which the weight vector $\vec{w}_m$ is applied to the data matrix $X_{nm}$ to reach the (predicted) output $\hat{\vec{y}}_n$, there is no constant offset term. It turns out that for data that are centered this offset term ("bias") is always zero and does not have to be included explicitly. Rather than applying equation 7, a more general predictive model that includes this bias can be written as:

$$\hat{\vec{y}}_n = X_{nm} \vec{w} + b \qquad (8)$$

where b is the bias term. Because we make it a practice to center the data first by Mahalanobis scaling, this bias term is zero and can be ignored.

When dealing with kernels, the situation is more complex, as they need some type of bias. We will give only a recipe here, that works well in practice, and refer to the literature for more details on why [11, 12, 16, 19]. Even when the data were Mahalanobis-scaled before applying a kernel transform, the kernel still needs some type of centering to be able to omit the bias term in the prediction model. A straightforward way for centering the kernel is to subtract the average from each column of the training data kernel, and store this average for later recall, when centering the test kernel. A second step for centering the kernel is going through the newly-obtained vertically centered kernel again, this time row by row, and subtracting the row average form each horizontal row.

The kernel of the test data needs to be centered in a consistent way, following a similar procedure. In this case, the stored column averages from the kernel of the training data will be used for the vertical centering of the kernel of the test data. This vertically-centered test kernel is then centered horizontally, i.e., for each row, the average of the vertically centered test kernel is calculated, and each horizontal entry of the vertically centered test kernel is substituted by that entry minus the row average.

The advantages of this algorithm for centering kernels as disclosed above is that it applies on rectangular data kernels as well. The flow chart for pre-processing the data, applying a kernel transform on this data, and then centering the kernel for the training data, validation data, and test data is shown in FIG. 10.

Both unsupervised and supervised learning methods were investigated. For unsupervised learning, Direct Kernel (DK)-SOMs were used, since SOMs are often applied for novelty detection and automated clustering. The DK-SOM used has a 9×18 hexagonal grid with unwrapped edges. For supervised learning, four kernel-based regression algorithms were used: classical Support Vector Machines effective in extracting relevant parameters from complex data spaces; kernel partial least square K-PLS, as proposed by Rosipal [10]; direct kernel partial least square (DK-PLS); and Least-Squares Support Vector Machines (i.e., LS-SVM, also known as kernel ridge regression).

Support Vector Machines or SVMs have proven to be formidable machine learning tools because of their efficiency, model flexibility, predictive power, and theoretical transparency [2,11,15]. While the nonlinear properties of SVMs can be exclusively attributed to the kernel transformation, other methods, such as self-organizing maps or SOMs [9], are inherently nonlinear because they incorporate various neighborhood-based manipulations. Unlike SVMs, the prime use for SOMs is often as a visualization tool [4] for revealing the underlying similarity/cluster structure of high-dimensional data on a two-dimensional map, rather than for regression or classification predictions.

Figures 4, 8:
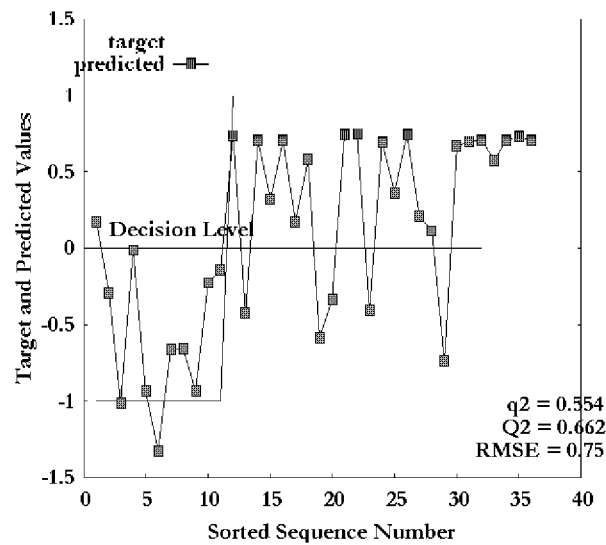
FIG. 4 is an error plot for 35 test cases, based on K-PLS for wavelet-transformed data.
FIG. 8 illustrates results for the prediction of ischemia using different techniques on the test data set.

The Analyze/StripMiner software package was used, developed in-house for the analysis [14], but SVMLib [1] for the SVM model was also used. Using the training set, the values for the parameters in DK-SOM, SVM, DK-PLS and LS-SVM were optimized before testing. The results are similar to the quality of classification achieved by the trained experts and similar for all tested methods, even though they use different data preprocessing. This is important because it indicates that there was no over-training in any of the tested methods. The agreement between DK-PLS, SVMLib, and LS-SVM is particularly good, and there are no noticeable differences between these methods on these data. The results are shown in FIGS. 2 and 3. FIG. 2 lists the number of correctly classified patterns and the number of misses for the negative and positive cases. FIG. 3 provides additional mesaures of quality of prediction. Further results are shown in FIG. 8. In FIG. 8, RMSE denotes the root mean square error (the smaller the better) and CC [%] means the percentage of correctly classified cases. The best result was obtained for the DK-PLS method, which also showed the best robustness. This already outperforms the predictive accuracy of three standard tests combined (ECG, ECHO, and Troponin I), which is 58% for these patients.

After tuning, the Parzen window width σ for SVM was chosen as 10. The regularization parameter, C, in SVMLib was set to 1/λ as suggested in [10]. Based on experience with other applications [14] and scaling experiments, ridge parameter λ was determined from the following equation, for an n data kernel:

$$\lambda = \min\left\{1; \left(\frac{n}{1500}\right)^{\frac{3}{2}}\right\} \tag{9}$$

More generally, empirically, we have found that λ is proportional to the number of data n to the power of 3/2.

The agreement between the direct kernel methods (DK-PLS and LS-SVM), K-PLS, and the traditional kernel-based SVM (SVMLib) indicates a near-optimal choice for the ridge parameter resulting from this formula.

Turning now to metrics for assessing the model quality, for a regression problem, another way to capture the error is by the Root Mean Square Error index or RMSE, which is defined as the average value of the squared error (either for the training set or the test set) according to:

$$RMSE = \sqrt{\frac{1}{n}\sum_i (\hat{y}_i - y_i)^2} \tag{10}$$

While the root mean square error is an efficient way to compare the performance of different prediction methods on the same data, it is not an absolute metric in the sense that the RMSE will depend on how the response for the data was scaled. In order to overcome this handicap, additional error measures were also used which are less dependent on the scaling and magnitude of the response value. A first metric used for assessing the quality of a trained model is $r^2$, which is defined as the squared coefficient of correlation between target values and predictions for the response according to:

$$r^2 = \frac{\sum_{i=1}^{n_{train}} (\hat{y}_i - \bar{y})(y_i - \bar{y})}{\sqrt{\sum_{i=1}^{n_{train}} (\hat{y}_i - \bar{y})^2} \sqrt{\sum_{i=1}^{n_{train}} (y_i - \bar{y})^2}} \tag{11}$$

where $n_{train}$ represents the number of data points in the training set. $r^2$ takes values between zero and unity, and the higher the $r^2$ value, the better the model. An obvious drawback of using $r^2$ for assessing the model quality is that it only expresses a linear correlation, indicating how well the predictions follow a line if $\hat{y}$ is plotted as function of y. While one would expect a nearly perfect model when $r^2$ is unity, this is not always the case. A second, and more powerful measure to assess the quality of a trained model is the so-called "Press r squared", or $R^2$, often used in chemometric modeling [6], where $R^2$ is defined as [7]:

$$R^2 = 1 - \frac{\sum_{i=1}^{n_{train}} (y_i - \hat{y}_i)^2}{\sum_{i=1}^{n_{train}} (y_i - \bar{y})^2} \tag{12}$$

$R^2$ is considered a better measure than $r^2$, because it accounts for the residual error as well. Just like $r^2$, $R^2$ ranges between zero and unity, and higher the value for $R^2$, better the model. The $R^2$ metric is generally smaller than $r^2$. For large datasets, $R^2$ tends to converge to $r^2$, and the comparison between $r^2$ and $R^2$ for such data often reveals hidden biases.

For assessing the quality of the validation set or a test set, we introduce similar metrics, $q^2$ and $Q^2$, where $q^2$ and $Q^2$ are defined as $1-r^2$ and $1-R^2$, respectively, for the data in the test set. For a model that perfectly predicts on the test data we would expect $q^2$ and $Q^2$ to be zero. The reason for introducing metrics which are symmetric between the training set and the test set is actually to avoid confusion. $Q^2$ and $q^2$ values apply to a validation set or a test set, and one would expect these values to be quite low in order to have a good predictive model. $R^2$ and $r^2$ values apply to training data, and it is easy to notice that if the predictions are close to actual values, they both are close to unity. Hence, any of them significantly different from 1 indicates a model with poor predictive ability.

Linear methods, such as partial-least squares, result in inferior predictive models as compared to the kernel methods. For K-PLS and DK-PLS, 5 latent variables were chosen, but the results were not critically dependent on the exact choice of the number of latent variables. Direct Kernel Principal Component Analysis (DK-PCA) was also tried, which is the direct kernel version of K-PCA [11-12,16], but the results were more sensitive to the choice of the number of principal components and not as good as the ones obtained using other direct kernel methods.

Typical prediction results for the magnetocardiogram data based on wavelet transformed data and DK-PLS are shown in FIG. 4. It can be seen from this figure that six data points are misclassified altogether in the predictions (one healthy or negative case and five ischemia cases). These cases were also difficult to identify correctly for the trained expert, based on a 2-D visual display of the time-varying magnetic field, obtained by proprietary methods.

For medical data, it is often important to be able to make a trade-off between false negative and false-positive cases, or between sensitivity and specificity (which are different metrics related to false positives and false negatives). In machine-learning methods, such a trade-off can easily be accomplished by changing the threshold for interpreting the classification. For example, in FIG. 4, rather than using zero as the discrimination value, one could shift the discrimination threshold towards a more desirable level, hereby influencing the false positive/false negative ratio.

Figure 5:
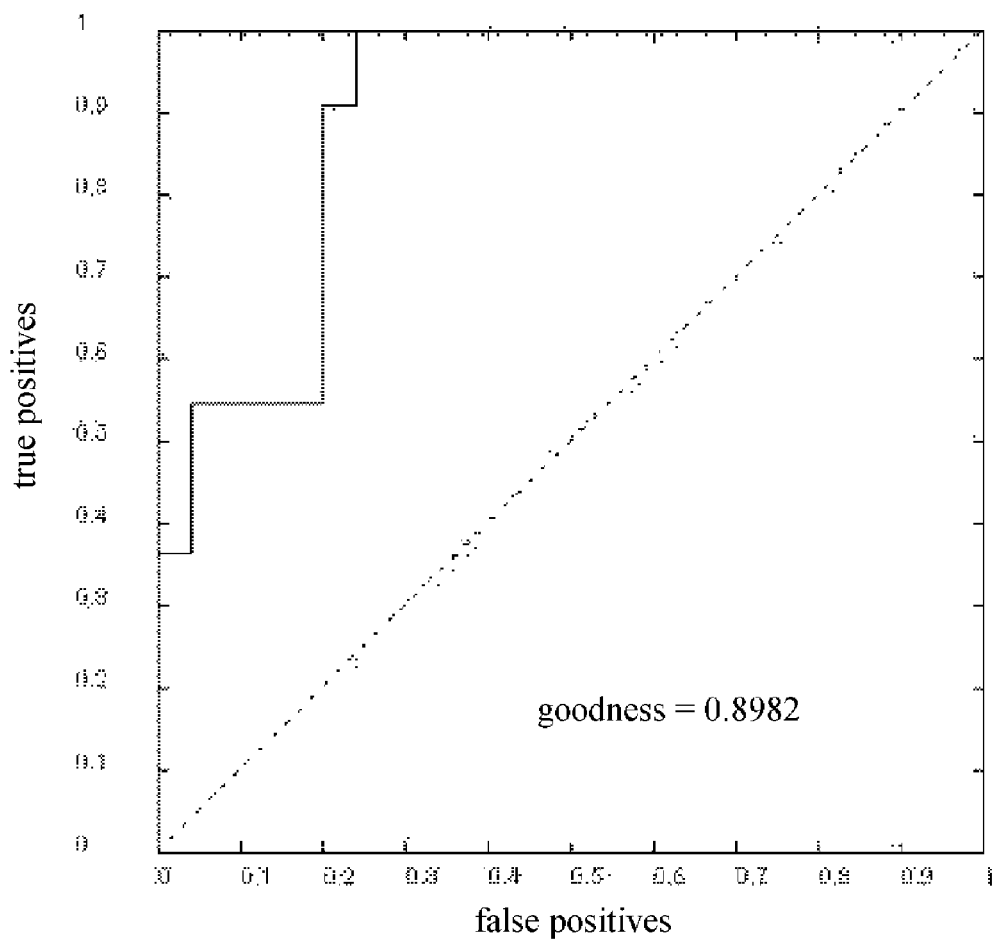
FIG. 5 is a receiver operator characteristics (ROC) curve showing possible trade-offs between false positive and false negatives.

A summary of all possible outcomes of such changes in the discrimination value can be displayed in an ROC curve, as shown in FIG. 5 for the above case. The concept of ROC curves (or Receiver Operator Characteristics) originated from the early development of the radar in the 1940's for identifying airplanes and is summarized in [13].

Figure 6:
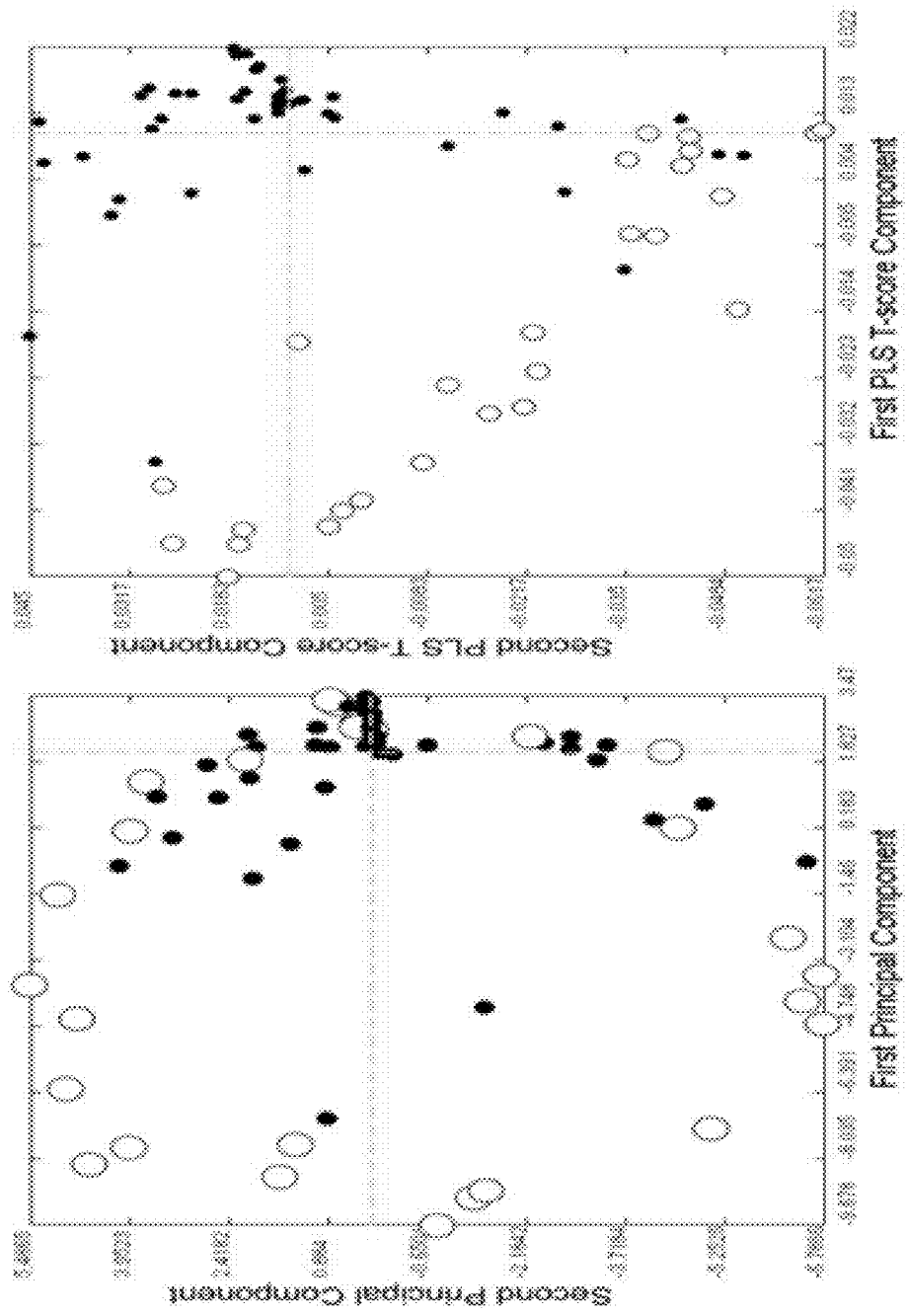
FIG. 6 is a Projection of 73 training data, based on (left) Direct Kernel Principal Component Analysis (DK-PCA), and (right) Direct Kernel PLS (DK-PLS). Diseased cases are shown as filled circles. The test data are not shown.

FIG. 6 displays a projection of 73 training data, based on (left) Direct Kernel Principal Component Analysis (DK-PCA), and (right) Direct Kernel PLS (DK-PLS). Diseased cases are shown as filled circles. The right side FIG. 6 shows a clearer separation and wider margin between different classes, based on the first two components for DK-PLS as compared to results of DK-PCA that are shown in the left side of FIG. 6. The test data, originally shown on these pharmaplots as dark and light crosses, shows an excellent separation between healthy and diseased cases for both methods.

Figure 7:
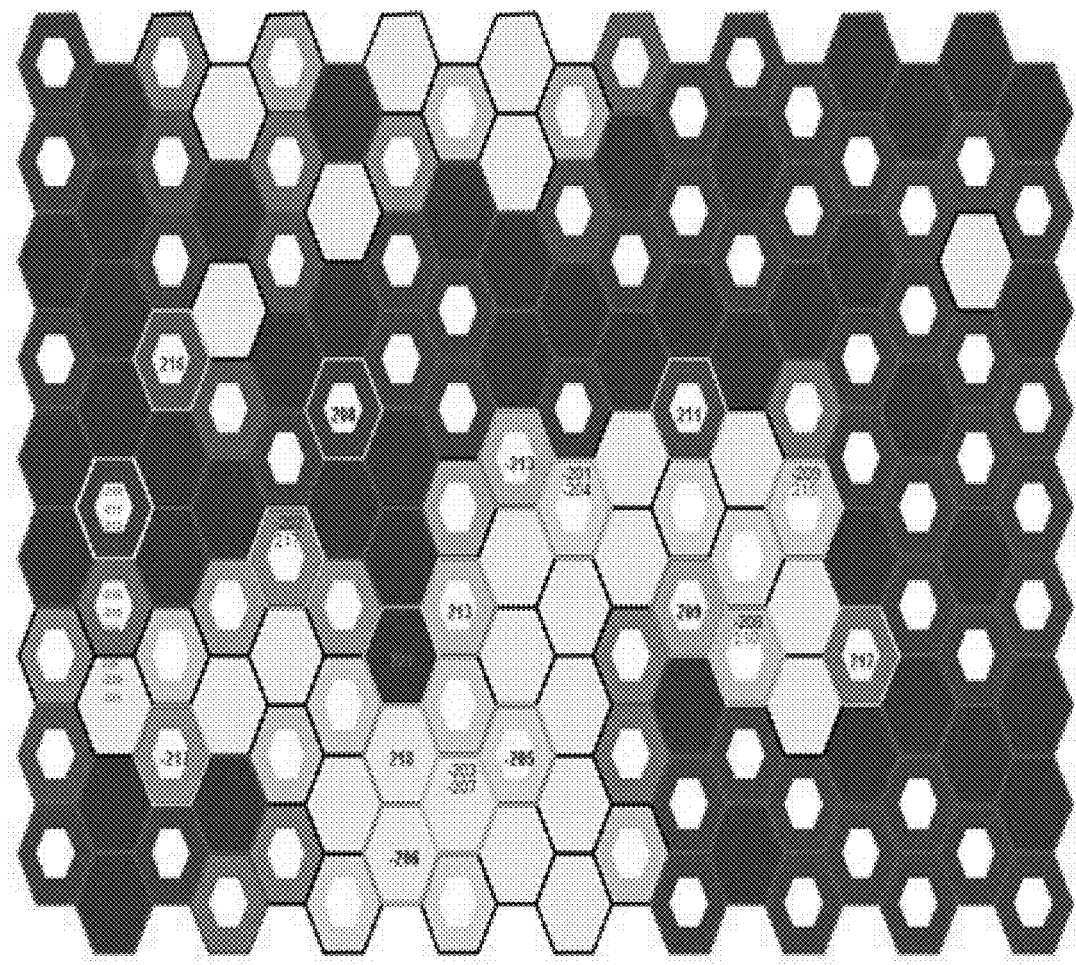
FIG. 7 illustrates test data displayed on a self-organizing map based on a 9×18 direct kernel self-organizing map (DK-SOM) in wrap-around mode.

A typical 9×18 self-organizing map on a hexagonal grid in wrap-around mode, based on the direct kernel SOM, is shown in FIG. 7. The wrap-around mode means that the left and right boundaries (and also the top and bottom boundaries) flow into each other, and that the map is an unfurling of a toroidal projection. The dark hexagonals indicate diseased cases, while the light hexagonals indicate healthy cases. Fully colored hexagons indicate the positions for the training data, while the white and dark-shaded numbers are the pattern identifiers for healthy and diseased test cases. Most misclassifications actually occur on boundary regions in the map. The cells in the map are colored by semi-supervised learning, i.e., each data vector, containing 36×32 or 1152 features, is augmented by an additional field that indicates the color. The color entry in the data vectors are updated in a similar way as for the weight vectors, but they are not used to calculate the distance metrics for determining the winning cell. The resulting maps for a regular SOM implementation are very similar to those obtained with the direct kernel DK-SOM. The execution time for generating DK-SOM on a 128 MHz Pentium III computer was 28 seconds, rather than 960 seconds required for generating the regular SOM, because the data dimensionality dropped to effectively 73 (the number of training data) from the original 1152, after the kernel transformation on the data. The fine-tuning for the SOM and DK-SOM was done in a supervised mode with learning vector quantization [9]. While the results based on SOM and DK-SOM are still excellent, they are not as good as those obtained with the other kernel-based methods (SVMLib, LS-SVM, and K-PLS).

Feature Selection

The results presented in the previous section were obtained using all 1152 (36×32) descriptors. It would be most informative to the domain expert, if one could identify where exactly in the time or wavelet signals and for which of the 36 magnetocardiogram signals that were measured at different positions for each patient the most important information necessary for good binary classification is located. Such information can be derived by feature selection.

Feature selection, i.e., the identification of the most important input parameters for the data vector, can proceed in two different ways: the filtering mode and the wrap-around mode. Ordinarily, these two approaches are employed separately from one another; however, they may also be combined within the scope of this disclosure and its associated claims.

In the filtering mode, features are eliminated based on a prescribed, and generally unsupervised procedure. An example of such a procedure could be the elimination of descriptor columns that contain four σ outliers, as is often the case in PLS applications for chemometrics. It is also common to drop "cousin" descriptors in a filtering mode, i.e., features that show more than 95% correlation with another descriptor. Depending on the modeling method, it is often common practice to drop the cousin descriptors and only retain the descriptors that (i) either show the highest correlation with the response variable, or (ii) have the clearest domain transparency to the domain expert for explaining the model.

The second mode of feature selection is based on the wrap-around mode. One wants to retain only the most relevant features necessary to have a good predictive model. Often, the modeling quality improves after the proper selection of the optimal feature subset. Determining the right subset of features can proceed based on different concepts, and the resulting subset of features is often dependent on the modeling method. Feature selection in a wrap-around mode generally proceeds by using a training set and a validation set, and the validation set is used to confirm that the model is not overtrained by selecting a spurious set of descriptors. Two generally applicable methods for feature selections are based on the use of genetic algorithms and sensitivity analysis.

The idea with the genetic algorithm approach is to be able to obtain an optimal subset of features from the training set, showing a good performance on the validation set as well.

The concept of sensitivity analysis [8] exploits the saliency of features, i.e., once a predictive model has been built, the model is used for the average value of each descriptor, and the descriptors are tweaked, one-at-a time between a minimum and maximum value. The sensitivity for a descriptor is the change in predicted response. The premise is that when the sensitivity for a descriptor is low, it is probably not an essential descriptor for making a good model. A few of the least sensitive features can be dropped during one iteration step, and the procedure of sensitivity analysis is repeated many times until a near optimal set of features is retained. Both the genetic algorithm approach and the sensitivity analysis approach are true soft computing methods and require quite a few heuristics and experience. The advantage of both approaches is that the genetic algorithm and sensitivity approach are general methods that do not depend on the specific modeling method.

Further Comments Regarding Machine Learning

Rather than reviewing here all available machine learning techniques, we first address the question why we didn't simply use support vector machines (SVMs), the state-of-the-art solution for both linear and non-linear problems. Scientifically, as noted earlier, the goal is to find a class of techniques that performs equally well on the given problem to ensure a stable solution. Within this class, the optimal model is then the one that is easiest to tune and that executes fastest. Comparing these models against SVMs as the standard helps verify the performance of any newly developed technique.

Regarding supervised learning, we give here a short description of the so called machine learning paradox in supervised learning, which is the reason for the multitude of models that were developed to find a way out of the dilemma.

It is customary to denote the data matrix as $X_{Nm}$ and the response vector as $\vec{y}_N$, assuming that there are N data points and m descriptive features in the dataset. We would like to infer $\vec{y}_N$ from $X_{Nm}$ by induction, denoted as $X_{Nm} \Rightarrow \vec{y}_N$, in such a way that our inference model derived from n training data points, but also does a good job on the out-of-sample data (i.e., N-n validation data and test data points). In other words, we aim at building a linear predictive model of the type:

$$\hat{\vec{y}}_n = X_{nm} \vec{w}_n \quad (13)$$

This equation assumes a known weight vector $\vec{w}_m$ that has to be determined in a prior step, the actual learning to satisfy, in the best case, equation:

$$X_{nm} \vec{w}_m = \vec{y}_n \quad (14)$$

Here, $X_{nm}$ are training data and $\vec{y}_n$ denotes the known answers ("labels").

Note that the data matrix is generally not symmetric. If that were the case, it would be straightforward to come up with an answer by using the inverse of the data matrix. We will therefore apply the pseudo-inverse transformation, which will generally not lead to precise predictions for y, but will predict y in a way that is optimal in a least-squares sense. The pseudo-inverse solution for the weight vector is illustrated below:

$$(X_{mn}^T X_{nm}) \vec{w}_m = X_{mn}^T \vec{y}_n$$

$$(X_{mn}^T X_{nm})^{-1} (X_{mn}^T X_{nm}) \vec{w}_m = (X_{mn}^T X_{nm})^{-1} X_{mn}^T \vec{y}_n$$

$$\vec{w}_m = (X_{mn}^T X_{nm})^{-1} X_{mn}^T \vec{y}_n$$

$$\vec{w}_m = (K_F)_{mm}^{-1} X_{mn}^T \vec{y}_n \quad (15)$$

$K_F = X^T_{mn} X_{nm}$ is the so-called "feature kernel matrix" and the reason for the machine learning paradox: Learning occurs only because of redundancies in the features—but then, $K_F$ is ill-conditioned (rank deficient). As indicated before, there are several ways to resolve the paradox:

1. By fixing the rank deficiency of $K_F$ with principal components (calculating the eigenvectors of the feature kernel) [18]
2. By regularization: use $K_F + \lambda I$ instead of $K_F$ (ridge regression) [17, 20-23]
3. By local learning We used four kernel-based regression algorithms: classical Support Vector Machines effective in extracting relevant parameters from complex data spaces [2, 12, 15], kernel partial least squares (K-PLS), as proposed by Rosipal [10], direct kernel partial least squares (DK-PLS), and Least-Squares Support Vector Machines (i.e., LS-SVM, also known as kernel ridge regression [24-28]). Additionally, we tested direct kernel principal component analysis (DK-PCA).

Partial least squares (PLS) is one of the standard analysis methods in QSAR and chemo metrics [29]. Kernel PLS (K-PLS) is a recently developed nonlinear version of PLS, introduced by Rosipal and Trejo [10]. K-PLS is functionally equivalent to SVMs but unlike SVMs, results turn out to be a bit more stable. K-PLS is currently used to predict binding affinities to human serum albumin.

In the work underlying this disclosure, we improved K-PLS to DK-PLS and made use of the earlier experiences developing the code for K-PLS, DK-PLS, DK-PCA, and LS-SVM in the Analyze/Stripminer program [14]. The difference between K-PLS and DK-PLS is that the feature (data) kernel matrix is used in K methods while this matrix is replaced by the (non-linear) kernel-transformed matrix in DK methods. For calculating the matrix inverse we applied Møller's scaled conjugate gradient method [30], which is implemented in the Analyze/Stripminer program.

Turning to unsupervised learning, we observe that the SOM [9, 17, 31-36] is an unsupervised learning neural network developed by Kohonen. The SOM is an iterative method based on competitive learning. It provides a mapping from a high-dimensional input data space into the lower dimensional output map, usually a one or two-dimensional map, see FIG. 11. Components (or data points) are loaded into the input layer and the SOM is trained using a competitive learning algorithm [4]. The weights are updated according to $$\vec{w}_m^{new} = (1-\alpha) \vec{w}_m^{old} + \alpha \vec{x}_m,$$

where $\alpha$ is the learning rate parameter. As the result of the learning the input data will be mapped onto the "winning" neuron. As a result of this process, the SOM is often used for dimension reduction and clustering. Moreover, a distinguishing feature of the SOM is that it preserves the topology of the input data from the high-dimensional input space onto the output map in such a way that relative distances between input data are more or less preserved [38]. Input data points that are located close to each other in the input space, are mapped to nearby neurons on the output map. SOM-based visualization methods are versatile tools for data exploration. They are used for clustering, correlation detection and projection of data [4,39].

The traditional SOM is a method based on the projection of the high-dimensional input data onto the lower-dimensional output map. Disclosed here, is a new kernel based SOM. The kernel SOM is now trained on the kernel representation of the data rather than on the original data. Using kernel transformed data here is not so much to "discover" non-linearities in the data because SOMs are inherently non-linear but to increase (learning) speed because the kernel has fewer effective features.

In summary, we have used and developed a set of machine learning tools that is presented in FIG. 12.

Conclusion

The binary classification of MCG data represents a challenging problem, but its solution is important if MCG is to succeed in clinical practice. Applying existing machine learning techniques such as SOM and SVM to MCG date results in a predictive accuracy of 74%. Very significant improvement is achieved by transforming the data first into the wavelet domain and additionally applying a kernel transform on wavelet coefficients, and by even applying the kernel transform alone without the wavelet transform. This increased the predictive accuracy to 83%.

The agreement of the results between kernel PLS (K-PLS) as proposed by Rosipal [10], direct kernel PLS (DK-PLS), support vector machine (SVMLib), and least square SVM (LS-SVM) is generally excellent. In this case, DK-PLS gave a superior performance, but the differences among kernel-based methods are not significant. This excellent agreement shows the robustness of the direct kernel methods. It could only be achieved if the selection of the ridge parameter by Equation (1) was nearly optimal. This selection defines also the regularization parameter, C, in support vector machines, when C is taken as $1/\lambda$.

The obtained results are meaningful for the medical community. DK-PLS was used to reach a sensitivity of 92% and a specificity of 75% for the detection of ischemia defined by coronary angiography. It is of notice that MCG is a purely functional tool that is sensitive for abnormalities in the electrophysiology of the heart and, therefore, can only diagnose the effect of a disease. The gold standard (coronary angiography), however, is a purely anatomical tool and diagnoses one cause of ischemic heart disease. Since MCG detects abnormalities that are not visible to the gold standard, it will always produce "false positives", which explains the comparatively low specificity in this application.

Note that the kernel transformation is applied here as a data transformation in a separate pre-processing stage. The data is actually replaced by a nonlinear data kernel and apply a traditional linear predictive model is then applied. Methods where a traditional linear algorithm is used on a nonlinear kernel transform of the data defined what is referred to here as "direct kernel methods." The elegance and advantage of such a direct kernel method is that the nonlinear aspects of the problem are captured in the kernel and are transparent to the applied algorithm.

While the kernels discussed herein are Gaussian in nature, this is exemplary, not limiting. For example, not limitation, so-called spline kernels may also be used and are regarded within the scope of this disclosure.

While only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

REFERENCES

[1] C.-C. Chang and C.-J. Lin, LibSVM, OSU, see http://www.csie.ntu.edu.tw/~cjlin/libsvmSVMLib.
[2] N. Cristianini and J. Shawe-Taylor [2000] *Support Vector Machines and Other Kernel-Based Learning Methods*, Cambridge University Press.
[3] I. Daubechies [1992], *Ten Lectures on Wavelets*, Siam, Philadelphia, Pa.
[4] G. Deboeck and T. Kohonen (Eds.) [1998] *Visual Explorations in Finance with Self-Organizing Maps*, Springer.
[5] V. Froelicher, K. Shetler, and E. Ashley [2002] "Better Decisions through Science: Exercise Testing Scores." *Progress in Cardiovascular Diseases*, Vol. 44(5), pp. 385-414.
[6] A. Golbraikh and A. Tropsha [2002] "Beware of $q^2$!" *Journal of Molecular Graphics and Modelling*, Vol 20, pp. 269-276.
[7] R. A. Johnson and D. W. Wichern [2000] *Applied Multivariate Statistical Analysis*, 2 ed., Prentice Hall.
[8] R. H. Kewley, and M. J. Embrechts [2000] "Data Strip Mining for the Virtual Design of Pharmaceuticals with Neural Networks," *IEEE Transactions on Neural Networks, Vol.* 11 (3), pp. 668-679.
[9] T. Kohonen [1997] *Self-Organizing Maps*, $2^{nd}$ Edition, Springer.
[10] R. Rosipal and L. J. Trejo [2001] "Kernel Partial Least Squares Regression in Reproducing Kernel Hilbert Spaces," *Journal of Machine Learning Research, Vol.* 2, pp. 97-128.
[11] B. Schölkopf and A. J. Smola [2002] *Learning with Kernels*, MIT Press.
[12] B. Schölkopf, A. Smola, and K-R Müller [1998] "Nonlinear Component Analysis as a Kernel Eigenvalue Problem," *Neural Computation*, Vol. 10, 1299-1319, 1998.
[13] J. A. Swets, R. M. Dawes, and J. Monahan [2000] "Better Decisions through Science," *Scientific American*, pp. 82-87.
[14] The Analyze/StripMiner, the description and the code are available at http://www.drugmining.com.
[15] V. Vapnik [1998] *Statistical Learning Theory*, John Wiley & Sons.
[16] W. Wu, D. L. Massarat and S. de Jong [1997] "The Kernel PCA Algorithm for Wide Data. Part II: Fast Cross-Validation and Application in Classification of NIR Data," *Chemometrics and Intelligent Laboratory Systems*, Vol. 37, pp. 271-280.
[17] A. E. Hoerl, and R. W. Kennard [1970] "Ridge Regression: Biased Estimation for Non-Orthogonal Problems," *Technometrics*, Vol. 12, pp. 69-82.
[18] J. Principe, N. R. Euliano, and W. C. Lefebre [2000] *Neural and Adaptive Systems: Fundamentals through Simulations*, John Wiley & Sons, Inc.
[19] W. Wu, D. L. Massarat and S. de Jong [1997] "The Kernel PCA Algorithm for Wide Data. Part I: Theory and Algorithms," *Chemometrics and Intelligent Laboratory Systems*, Vol. 36, pp. 165-172.
[20] Vladimir Cherkassky and Filip Mulier [1998] *Learning from Data: Concepts, Theory, and Methods*, John Wiley & Sons, Inc.
[21] S. Haykin [1999] *Neural Networks: A Comprehensive Foundation* ($2^{nd}$ Ed.), Prentice Hall.
[22] A. N. Tikhonov [1963] "On Solving Incorrectly Posed Problems and Method of Regularization," *Doklady Akademii Nauk USSR*, Vol. 151, pp. 501-504.
[23] A. N. Tikhonov and V. Y. Arsenin [1977] *Solutions of ill-Posed Problems*, W. H. Winston, Washington D.C.
[24] Evgeniou, T., Pontil, and M. Poggio, T. [2000] "Statistical Learning Theory: A Primer," *International Journal of Computer Vision*, Vol. 38(1), pp. 9-13.
[25] T. Evgeniou, M. Pontil, and T. Poggio [2000] "Regularization Networks and Support Vector Machines," in *Advances in Large Margin Classifiers*, MIT Press.
[26] Poggio, T., and Smale S., [2003] "The Mathematics of Learning: Dealing with Data," To appear in *Notices of the AMS*, May 2003.
[27] Suykens, J. A. K. and Vandewalle, J. [1999] "Least-Squares Support Vector Machine Classifiers," *Neural Processing letters*, Vol. 9(3), pp. 293-300, Vol. 14, pp. 71-84.
[28] Suykens, J. A. K., van Gestel, T. de Brabanter, J. De Moor, M., and Vandewalle, J. [2003] *Least Squares Support Vector Machines*, World Scientific Pub Co, Singapore.
[29] Svante Wold, Michael Sjöstrom, and Lennart Eriksson [2001] "PLS-Regression: a Basic Tool of Chemometrics," *Chemometrics and Intelligent Laboratory Systems*, 58:109-130.

[30] Møller, M. F., [1993] "A Scaled Conjugate Gradient Algorithm for Fast Supervised Learning," *Neural Networks*, Vol. 6, pp. 525-534.

[31] H. Ritter, T. Kohonen, "Self-Organizing Semantic Maps," Biological Cybernetics, vol. 61, pp. 241-254, 1989.

[32] T. Kohonen, Self Organization and Associative Memory, 2nd ed., Springer-Verlag, 1988.

[33] T. Kohonen, "The Self-Organizing Map," Neurocomputing, 21(1): 1-6, November 1998.

[34] T. Kohonen, "Thing You Haven't Heard about the Self-Organizing Map," IEEE International Conference on Neural Network, vol. 3, pp. 1147-1156, 1993.

[35] T. Kohonen, "Generalization of the Self-Organizing Map," International Joint Conference on Neural Networks, vol. 1, pp. 21-26, 1993.

[36] G. Deboeck and T. Kohonen, Visual Explorations in Finance with Self-Organizing Maps, Springer, 2000.

[37] H. C. Card, G. K. Rosendakl, D. K. Mcneill, and R. D. Mcleod, "Competitive Learning Algorithms and Neurocomputer Architecture," IEEE Transactions on Computers, vol. 47, no. 8, pp. 847-858, August 1998.

[38] J. S. Kirk, and J. M. Zurada, "Motivation for Genetically-Trained Topography-Preserving Map," International Joint Conference on Neural Networks 2002, vol. 1, pp. 394-399, 2002.

[39] J. Vesanto, J. Himberg, M. Siponen, and A. Ollisimula, "Enhancing SOM Based Data Visualization," Proceedings of the International Conference on Soft Computing and Information/Intelligent Systems, pp. 64-67, 1998.

[40] G. Stroink, W. Moshage, S. Achenbach: "Cardiomagnetism". In: *Magnetism in Medicine*, W. Andrä, H. Nowak, eds. Berlin: Wiley VCH; 1998; 136-189.

[41] M. Mäkijärvi, J. Montonen, J. Nenonen: "Clinical application of magnetocardiographic mapping" in: *Cardiac mapping, M. Shenasa, M. Borgreffe, G. Breithardt, Eds. Mount Kisco, N.Y.: Futura Publishing Co*, 2003.

[42] M. Mäkijärvi, K. Brockmeier, U. Leder, et al.: "New trends in clinical magnetocardiography". In *Biomag*96: *Proc. of the* 10*th Internat. Conf. on Biomagnetism*, Aine C., et al., eds., New York: Springer, 2000; 410-417.

We claim:

1. A method for automating the identification of meaningful features and the formulation of expert rules for classifying magnetocardiography data, comprising:
applying a kernel transform to sensed data acquired from sensors sensing magnetic fields generated by a patient's heart activity, resulting in transformed data; and
identifying said meaningful features and formulating said expert rules from said transformed data, using machine learning.

2. The method of claim 1, said kernel transform satisfying Mercer conditions.

3. The method of claim 1, said kernel transform comprising a radial basis function.

4. The method of claim 1, said applying a kernel transform comprising:
assigning said transformed data to a first hidden layer of a neural network;
applying training data descriptors as weights of said first hidden layer of said neural network; and
calculating weights of a second hidden layer of said neural network numerically.

5. The method of claim 1, further comprising:
classifying said transformed data using direct kernel partial least square (DK-PLS) machine learning.

6. The method of claim 1, further comprising transforming said sensed data into wavelet domain data prior to applying said kernel transform by:
applying a Daubechies wavelet transform to said sensed data.

7. The method of claim 6, further comprising:
selecting features from said wavelet domain data which improve said classification of magnetocardiography data.

8. The method of claim 1, further comprising:
normalizing said sensed data.

9. The method of claim 8, said normalizing said sensed data comprising:
Mahalanobis scaling said sensed data.

10. The method of claim 1, further comprising:
centering a kernel of said kernel transform.

11. An apparatus for automating the identification of meaningful features and the formulation of expert rules for classifying magnetocardiography data, comprising computerized storage, processing and programming for:
applying a kernel transform to sensed data acquired from sensors sensing magnetic fields generated by a patient's heart activity, resulting in transformed data; and
identifying said meaningful features and formulating said expert rules from said transformed data, using machine learning.

12. The apparatus of claim 11, wherein kernel transform satisfies Mercer conditions.

13. The apparatus of claim 11, said kernel transform comprising a radial basis function.

14. The apparatus of claim 11, said computerized storage, processing and programming for applying a kernel transform further comprising computerized storage, processing and programming for:
assigning said transformed data to a first hidden layer of a neural network;
applying training data descriptors as weights of said first hidden layer of said neural network; and
calculating weights of a second hidden layer of said neural network numerically.

15. The apparatus of claim 11, further comprising computerized storage, processing and programming for:
classifying said transformed data using direct kernel partial least square (DK-PLS) machine learning.

16. The apparatus of claim 11, further comprising using said computerized storage, processing and programming for transforming said sensed data into wavelet domain data prior to applying said kernel transform by:
applying a Daubechies wavelet transform to said sensed data.

17. The apparatus of claim 16, further comprising using said computerized storage, processing and programming for:
selecting features from said wavelet domain data which improve said classification of magnetocardiography data.

18. The apparatus of claim 11, further comprising computerized storage, processing and programming for:
normalizing said sensed data.

19. The apparatus of claim 18, said computerized storage, processing and programming for normalizing said sensed data comprising computerized storage, processing and programming for:
Mahalanobis scaling said sensed data.

20. The apparatus of claim 11, further comprising computerized storage, processing and programming for:
centering a kernel of said kernel transform.

* * * * *